United States Patent [19]

Frigerio et al.

[11] Patent Number: 4,971,984

[45] Date of Patent: Nov. 20, 1990

[54] 2-METHYLTHIOMETHYL-DIHYDROPYRIDINES AND PHARMACEUTICAL COMPOSITIONS CONTAINING THEM

[75] Inventors: Marco Frigerio; Andrea Zaliani; Carlo Riva; Carmelo Gandolfi; Odoardo Tofanetti; Sergio Tognella, all of Milan, Italy

[73] Assignee: Beehringer Biochemia Robin S.p.A., Milan, Italy

[21] Appl. No.: 131,393

[22] Filed: Dec. 10, 1987

[30] Foreign Application Priority Data

Dec. 11, 1986 [IT] Italy ............................. 22648 A/86

[51] Int. Cl.⁵ .................. A61K 31/455; C07D 211/86
[52] U.S. Cl. .................... 514/356; 514/333; 514/341; 546/321; 546/263; 546/278
[58] Field of Search ............... 546/321, 263, 278; 514/356, 333, 341

[56] References Cited

U.S. PATENT DOCUMENTS

| | | | |
|---|---|---|---|
| 4,430,333 | 2/1984 | Campbell et al. | 546/321 |
| 4,492,703 | 1/1985 | Goldmann et al. | 546/321 |
| 4,515,799 | 5/1985 | Campbell et al. | 546/270 |
| 4,532,248 | 7/1985 | Franckowiak et al. | 546/116 |
| 4,572,909 | 2/1986 | Campbell et al. | 546/321 |
| 4,590,195 | 5/1986 | Alker et al. | 546/321 |
| 4,654,353 | 3/1987 | Alker et al. | 546/321 |
| 4,732,985 | 3/1988 | Alker et al. | 546/321 |

FOREIGN PATENT DOCUMENTS

| | | |
|---|---|---|
| 0095450 | 11/1983 | European Pat. Off. |
| 0165032 | 12/1985 | European Pat. Off. |
| 0200524 | 11/1986 | European Pat. Off. |
| 0206747 | 12/1986 | European Pat. Off. |
| 0221720 | 5/1987 | European Pat. Off. |
| 0222598 | 5/1987 | European Pat. Off. |
| 0225175 | 6/1987 | European Pat. Off. |
| 8700836 | 2/1987 | World Int. Prop. O. |

OTHER PUBLICATIONS

Schramm et al., Nature, vol. 303, June 9, 1983.

Primary Examiner—Jane T. Fan
Attorney, Agent, or Firm—Armstrong, Nikaido, Marmelstein, Kubovcik & Murray

[57] ABSTRACT

Compounds of formula I

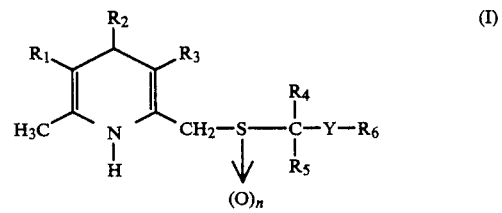

wherein
$R_1$ is a cyano, nitro, benzoyl, acetyl, amido or alkoxycarbonyl group;
$R_2$ is substituted aryl- or heterocyclic residue;
$R_3$ is alkoxycarbonyl group;
$R_4$ and $R_5$, being the same or different, are hydrogen, alkyl, aryl or heterocyclic groups;
Y is oxygen, sulphur or substituted or unsubstituted nitrogen atom, that can be a part of a heterocyclic ring;
n is 0, 1 or 2
$R_6$ and $R_{10}$, that can be the same or different, are: hydrogen; $C_1$–$C_6$-alkyl optionally substituted by hydroxy, amino, monoalkyl and dialkylamino, $C_1$–$C_6$-alkoxy, $C_1$–$C_6$-alkoxycarbonyl, $C_1$–$C_3$-carbonyloxy, aryl, heteroaryl and cycloalkyl; a $C_1$–$C_{12}$-alkanoyl, aroyl or heteroaryl group optionally substituted by halogen, nitro, amino monoalkylamino, dialkylamino, hydroxy, $C_1$–$C_6$-alkoxy, $C_1$–$C_6$-alkoxycarbonyl, $C_1$–$C_6$-alkylthio, $C_1$–$C_3$-carbonyloxy, aryl, heteroaryl, cycloalkyl groups.

These compounds are useful in therapy as cardiovascular agents.

6 Claims, No Drawings

2-METHYLTHIOMETHYL-DIHYDROPYRIDINES AND PHARMACEUTICAL COMPOSITIONS CONTAINING THEM

The present invention concerns methylthiomethyl-1,4-dihydropyridines, a method for their preparation and pharmaceutical compositions containing them.

The compounds of the present invention are represented by the formula:

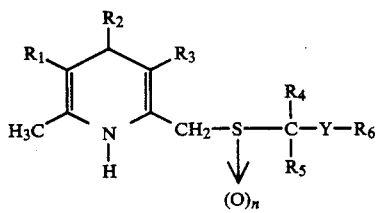

wherein:
$R_1$ is acetyl, benzoyl, cyano, nitro, a $COOR_7$ or a $CONR_8R_9$ group:
$R_2$ is:
  (a) a phenyl group that can be unsubstituted or substituted with one or more $C_1$–$C_6$-alkoxy, halo-$C_1$–$C_6$-alkyl, halogen, nitro, cyano, $C_1$–$C_6$-alkyl, halo-$C_1$–$C_6$-alkoxy, $C_1$–$C_6$-alkoxycarbonyl, $C_1$–$C_6$-alkylthio, $C_1$–$C_6$-alkylsulphinyl groups;
  (b) pentafluorophenyl;
  (c) α and β-naphtyl;
  d) a 5- or 6-membered heterocyclic ring;
$R_3$ is a $COOR_7$ group;
$R_4$ and $R_5$, that can be the same or different, are: hydrogen; $C_1$–$C_6$-alkyl; phenyl unsubstituted or substituted by one or more groups selected from halogen, nitro, $C_1$–$C_6$-alkoxy, $C_1$–$C_6$-alkoxycarbonyl, amino, mono or dialkylamino, dialkylamino methyl, hydroxy; $COOR_7$ groups; $C_3$–$C_7$-cycloalkyl; 5 or 6 membered heterocyclic rings, containing one or more O, S, or N atoms; or $R_4$ and $R_5$, together with the carbon atom to which they are bound, form a 5 or 6 membered ring;
Y is oxygen, sulphur or a $>NR_{10}$ group;
$R_6$ and $R_{10}$, that can be the same or different, are: hydrogen; $C_1$–$C_6$-alkyl optionally substituted by hydroxy, amino, monoalkyl or dialkylamino, $C_1$–$C_6$-alkoxy, $C_1$–$C_6$-alkoxycarbonyl, $C_1$–$C_3$-carbonyloxy, aryl, heteroaryl or $C_3$–$C_7$-cycloalkyl; a $C_1$–$C_{12}$-alkanoyl, aroyl or heteroaroyl group optionally substituted by halogen, nitro, amino, monoalkylamino, dialkylamino, hydroxy, $C_1$–$C_6$-alkoxy, $C_1$–$C_6$-alkoxycarbonyl, $C_1$–$C_6$-alkylthio, $C_1$–$C_3$-carbonyloxy, aryl, heteroaryl, $C_3$–$C_7$-cycloalkyl groups; aryl or 5-6-membered heteroaryl group, containing one or more O, S or N atoms, optionally substituted by one or more halogen, nitro, cyano, $C_1$–$C_6$-alkoxycarbonyl, hydroxy, $C_1$–$C_3$-alkylcarbonylamino, monoalkylamino, dialkylamino, SH, $C_1$–$C_6$-alkylthio, $C_1$–$C_6$-alkylsulphinyl; or $R_6$ and $R_{10}$, taken together with the nitrogen atom to which they are bound, form a pyrrolyl, piperidyl, morpholyl, piperazinyl, succinimidyl or phtaloyl ring;
$R_7$ is a $C_1$–$C_6$-alkyl group, optionally substituted by hydroxy, amino, monoalkylamino, dialkylamino or $C_1$–$C_6$-alkoxy; $C_3$–$C_6$-alkenyl group; optionally substituted phenyl group;
$R_8$ and $R_9$, that can be the same or different, are: hydrogen; $C_1$–$C_6$-alkyl; benzyl or aryl;
n is 0, 1 or 2, with the proviso that, when Y is S, n is zero.

Pharmaceutically acceptable salts, optical antipodes, i.e. the single enantiomers, racemic mixtures of optical antipodes, the single diasteroisomers and mixtures of diastereoisomers of compounds of formula I are also included in the scope of the present invention.

Pharmaceutically acceptable salts of compounds I are those including pharmaceutically acceptable acids and bases.

Dihydropyridines having a dithioketalic structure are already disclosed by E.P. 0095450 of 13.5.1983 in the name of AB Astra. Said products are not only structurally different from compounds described in the present patent application, but they are also provided with a different pharmacological activity.

Alkyl, alkenyl, acyloxy, acylthio and acylamino groups of the compounds of the invention may have both a linear or branched chain.

A halo-$C_1$–$C_6$-alkyl group is preferably a trichloromethyl or trifluoromethyl group.

A halo-$C_1$–$C_6$-alkoxy group is preferably difluoromethoxy.

A $C_1$–$C_6$-alkyl group is preferably methyl, ethyl, isopropyl or terbutyl.

A $C_3$–$C_6$ alkenyl group is preferably allyl

An aryl group is preferably phenyl.

A heteroaryl group is preferably α or β-pyridyl.

A $C_1$–$C_{12}$-alkanoyl group is preferably formyl, acetyl or butyroyl.

A $C_3$–$C_7$-cycloalkyl group is preferably cyclopropyl, cyclopentyl or cyclohexyl.

A 5- or 6-membered heterocyclic ring is preferably pyrrol, pyrrolidine, piperidine, piperazine, morpholine, succinimide, phtalamide or imidazole.

An aroyl group is preferably benzoyl, p-amino-benzoyl or o-hydroxy-benzoyl.

An heteroaroyl group is preferably nicotinoyl, 5-bromo-nicotinoyl, imidazolyl-1-carbonyl.

A monoalkylamino group is preferably methyl-, ethyl-, isopropyl or benzylamino.

A dialkylamino group is preferably dimethyl-, diethyl-, N-methyl-N-benzylamino or a group wherein the alkyl substituents are included in a heterocyclic ring such as pyrrolidin-1-yl, piperidin-1-yl, piperazin-1-yl, 4-substituted-piperazin-1-yl, imidazol-1-yl, morpholin-4-yl. Particularly preferred compounds are those wherein n=0. A preferred group of compounds of formula I are compounds wherein
$R_1$ is nitro or an $C_1$–$C_6$-alkoxycarbonyl group,
$R_2$ is a phenyl group substituted by nitro, trifluoromethyl, methylthio or one or more times by halogen,
$R_3$ is an $C_1$–$C_6$-alkoxycarbonyl group,
$R_4$ and $R_5$ that can be the same or the different, are hydrogen, methyl, p-nitrophenyl or a $C_1$–$C_6$-alkoxycarbonyl group
Y is oxygen, sulphur or a $NR_{10}$ group
$R_6$ and $R_{10}$ that can be the same or different are hydrogen, $C_1$–$C_6$-alkyl, optionally substituted by methoxyethoxy or phenyl, acetyl, benzoyl, optionally substituted by hydroxy or amino, phenyl, nicotinoyl, 5-bromo-nicotinoyl, N-imidazolylcarbonyl, $C_1$–$C_6$-alkoxycarbonyl or β-pyridyl, Specific examples of compounds of the invention of formula I are listed in the following Table.

TABLE I

| R₁ | R₂ | R₃ | R₄ | R₅ | Y | R₆ | n |
|---|---|---|---|---|---|---|---|
| COOEt | m-NO₂—C₆H₄ | COOEt | H | H | O | H | 0 |
| COOMe | m-Cl—C₆H₄ | COOMe | H | H | O | CH₃ | 0 |
| COOEt | m-NO₂—C₆H₄ | COOEt | H | H | S | CH₃ | 0 |
| NO₂ | m-CF₃—C₆H₄ | COOEt | H | H | O | H | 0 |
| COOEt | m-NO₂—C₆H₄ | COOEt | H | COOMe | O | H | 0 |
| COOEt | m-NO₂—C₆H₄ | COOEt | H | p-NO₂C₆H₄ | O | H | 0 |
| COOMe | o-CF₃—C₆H₄ | COOEt | H | H | S | CH₂∅ | 0 |
| COOEt | m-NO₂—C₆H₄ | COOEt | CH₃ | CH₃ | O | CH₃ | 0 |
| COOEt | m-NO₂—C₆H₄ | COOEt | H | H | O | COCH₃ | 0 |
| COOEt | m-NO₂—C₆H₄ | COOEt | H | H | NH | COCH₃ | 0 |
| COOEt | m-NO₂—C₆H₄ | COOEt | H | H | O | —C(=O)—C₆H₄-p-NH₂ | 0 |
| COOMe | m-Cl—C₆H₄ | COOMe | H | H | O | C₆H₅ | 0 |
| COOC₃H₇-i | o-SCH₃C₆H₄ | COOMe | H | H | S | C₆H₄-p-Cl | 0 |
| COOMe | m-NO₂—C₆H₄ | COOEt | H | H | O | β-pyridyl | 0 |
| COOMe | m-Cl—C₆H₄ | COOEt | H | H | NH | —C(=O)—C₆H₅ | 0 |
| COOEt | m-NO₂—C₆H₄ | COOEt | H | H | NH | —C(=O)—C₆H₄-p-NH₂ | 0 |
| COOEt | m-NO₂—C₆H₄ | COOEt | H | H | O | CH₂OCH₂CH₂OCH₃ | 0 |
| COOMe | m-CF₃—C₆H₄ | COOC₃H₇-i | H | H | O | —C(=O)—OEt | 0 |
| COOC₂H₄OCH₃ | o-Cl—C₆H₄ | COOMe | H | H | S | COCH₃ | 0 |
| COOEt | m-NO₂—C₆H₄ | COOEt | H | H | NH | —C(=O)—C₆H₄-o-OH | 0 |
| COOEt | m-NO₂—C₆H₄ | COOEt | H | H | O |  | 0 |
| COOEt | m-NO₂—C₆H₄ | COOEt | H | H | O | 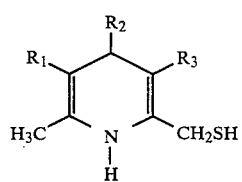 | 0 |
| COOMe | m-Cl—C₆H₄ | COOMe | H | H | NH | —C(=O)-(3-pyridyl) | 0 |
| COOEt | m-NO₂—C₆H₄ | COOEt | H | H | O | COCH₃ | 1 |
| COOEt | m-NO₂—C₆H₄ | COOEt | H | H | O | COCH₃ | 2 |

The compounds of the inventions are prepared by reacting a 1-mercaptomethyl-1,4-dihydro-pyridine of general formula II $$\text{(II)}$$

wherein $R_1$, $R_2$ and $R_3$ are as above defined, with a compound of general formula III:

$$\text{(III)}$$

wherein $R_4$ and $R_5$ are as above defined and A and B, that are the same or different, are halogen (preferably chlorine), hydroxy, $C_1$-$C_4$-alkoxy group or Y—$R_6$, wherein $R_6$ is as above defined, or together with the carbon they are linked with, form a carbonyl group to give a compound of general formula Ia

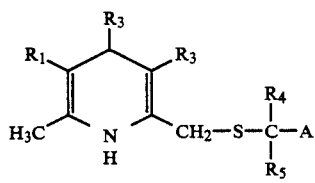

wherein $R_1$, $R_2$, $R_3$, $R_4$, $R_5$ and A are as above defined. The compounds of formula Ia are optionally converted by oxidative processes to give compound I wherein n is 1 or 2, or optionally etherified or esterified to other compounds I by known procedures.

The condensation reaction of a compound II with a compound III is usually carried out in an inert solvent such as a lower alcohol, e.g. methanol, ethanol, isopropanol; an ether, such as dioxane, tetrahydrofuran, dimethoxyethane; or in mixtures thereof, at a temperature ranging from 0° C. to the solvent's reflux temperature, for reaction times ranging from a few minutes to 90 hours.

The reaction is carried out in the presence of a condensing agent; for instance, when A is hydroxy or $C_1$–$C_4$-alkoxy, it is preferable to operate in the presence of an acid catalyst, such as, for instance, an inorganic acid, e.g. hydrochloric or sulphuric acid or an organic acid, acetic, benzoic, p-toluensulphonic, sulphosalicylic acid. When A is halogen, it is necessary to operate in the presence of a base, such as, for instance, potassium t-butylate, sodium ethylate, sodium hydride, triethylamine, diaza-[2,2,2]-bicyclooctane, pyridine, potassium carbonate.

The thioether bond of a compound of formula I, wherein Y is different from sulphur, may be selectively oxidized to sulphoxide or sulphone according to known methods. Selective oxidation to a sulphoxide is carried out using a molar equivalent of an organic peracid such as, for instance, peracetic, perbenzoic, m-chloroperbenzoic, monoperphthalic, trifluoroperacetic, performic acid or using periodic acid or a salt thereof.

If two or more molar equivalents of said peracids are used, the oxidation to sulphone is obtained.

Suitable solvents for said reaction are those which are inert under the used oxidation conditions, such as, for instance, alcohols, e.g. methanol or ethanol; esters, e.g. ethyl acetate or chlorinated solvents such as dichloromethane, or mixtures thereof.

The reaction temperature ranges from 0° C. to the room temperature and the reaction times range from a few minutes to several hours.

The 1,4-dihydropyridine ring is not oxidized to pyridine in the above conditions.

Subsequent optional alkylation or acylation reactions of compounds V to compounds Ia are carried out according to known techniques.

The compounds II are described and claimed in WO/PCT/87/00445.

The compounds of the invention of formula I protect cellular membranes from oxidative injuries; a reduced malondialdehyde formation is observed after incubation of rat erithrocyte membranes (M. Aishita et al., Arch. Intern. Pharmacodyn. 261, 316, 1983) and of rat brain homogenate (Stocks et al., Clin. Sci. Molec. Med., 47, 215, 1974) with the compounds of the invention.

Sudden death induced by bolus of arachidonic acid or of a mixture of ADP and collagen, in mice and rabbits is prevented by previous oral and/or intraperitoneal treatment with the compounds of formula I.

The compounds of the invention of formula I inhibit the release of proteinase from human leucocytes challenged by anti-Ig-E-antibody, when tested "in vitro" after 30' of preincubation time.

The compounds of the invention are useful for the control of electrolyte fluxes through membranes of blood cellular components such as platelets, leukocytes, erythrocytes and for the regulation of their deformability and reactivity against excitatory stimuli. At the cellular level, they are also useful in the control of enzymatic processes involving both activation and inhibition of calcium-dependent enzymes.

The compounds of the invention were also tested, according to the Godfraind's procedure (T. Godfraind et al., Arch. Intern. Pharmacol., 172, 235, 1968), to evaluate their property of inhibiting the contraction induced by $CaCl_2$ in $K^+$-depolarized aorta strips.

When the standard incubation times are used (2–15 minutes) some of the compounds show $ID_{50}$ ranging from $10^{-6}$ to $10^{-8}M$, while when the incubation times are prolonged to 2–3 hours the same compounds show $ID_{50}$ values, ranging from $10^{-8}$ to $10^{-10}M$.

The compounds of the inventions are able to reduce mean blood pressure, when administered to spontaneously hypertensive rats by oral route.

The compounds of invention are therefore useful in the treatment of thromboembolic disorders, in myocardial, renal and cerebral ischemia and in the treatment of hypertensive disorders.

For the planned therapeutical use, the compounds of the invention may be administered pure or as pharmaceutical compositions by oral, parenteral or rectal route.

Said pharmaceutical compositions, that are also object of the present invention, may be prepared according to known techniques, such as those described in "Remington's Pharmaceutical Sciences Handbook", Hack Publishing Co., U.S.A..

The amount of active principle administered by oral route may vary from 0.01 mg/kg to 10 mg/kg, preferably from 0.05 mg/kg to 5 mg/kg per day.

The amount of active principle administered by parenteral route will vary from 0.001 mg/kg to 5 mg/kg and preferably from 0.01 mg/kg to 2 mg/kg per day.

A unit dosage for oral administration may contain from 0.05 to 70 mg of active principle.

The compounds of the invention may be administered once or twice a day, but repeated administrations may be convenient, at least sometimes, and may vary in accordance with the conditions of the patient and the chosen administration route. In the present case, the term "patient" means a warm-blooded animal, man included. For the oral administration, the compound may be administered as solid or liquid preparation (capsules, pills, tablets, powders, solutions, suspensions or emulsions). The preferred formulations are hard or soft gelatin capsules, containing lubricants and inert excipients e.g. lactose, saccharose, and starch, or tablets containing conventional excipients such as lactose, saccharose, starch, gelatin, alginic acid, stearic acid, magnesium stearate, etc.

For the parenteral administration, the compounds may be formulated as suspensions or solutions in diluents or physiologically acceptable vehicles, such as water, vegetal, animal, mineral or synthetic oils, aqueous solutions of mineral salts, dextrose and other sugars, ethanol or glycols such as propylen- or polyethylenglycols.

For rectal administration the most convenient formulation are suppositories, prepared with conventional vehicles such as cocoa butter, wax, polyvinylpyrrolidone or polyoxyethylenglycol and derivatives thereof.

The preferred administration route is the oral route.

The following examples illustrate, but do not limit the invention.

EXAMPLE 1

2 g of 3,5-dicarboethoxy-6-methyl-2-(mercaptomethyl) -4-(m-nitrophenyl)-1,4-dihydropyridine (4,92 mmol.) and 20 mg of 2-sulphosalicylic acid bihydrate (0,049 mmol.) are dissolved in 20 ml of 2,2-dimethoxy-propane. The solution is stirred for 2 hours at room temperature, then the solvent is evaporated under reduced pressure. The residue is dissolved in ethyl acetate, washed with a NaHCO$_3$ solution (5%, 2×10 ml) and water (3×20 ml), dried on Na$_2$SO$_4$ and evaporated at reduced pressure. 1.8 g of 3,5-dicarboethoxy-6-methyl-2-[2-methoxyprop-2-yl-thiomethyl]-4-(m-nitrophenyl)-1,4-dihydropyridine (thick yellow oil) are obtained.

NMR ($\delta$ CDCl$_3$)$_3$, 1.2 (t, 6H), 1.25 (s, 6H), 2.33 (s, 2H), 3.30 (s, 3H), 4.15 (q, 4H), 4.22 (s, 2H), 5.10 (s, 1H), 7.20–8.20 (m, 5H).

Following the same procedure, but using p-NO$_2$-benzaldehyde diethylacetal, 1,1-dimethoxy-cyclohexane, 1,1-dimethoxy-1-phenyl-ethane, 3-pyridine carboxyaldehyde diethylacetal, and a suitable 2-mercaptomethyl-1,4-dihydropyridine, the following compounds are obtained:

3,5-dicarboethoxy-6-methyl-4-(m-nitrophenyl)-2-[-1-ethoxy -1-(p-NO$_2$-phenyl)methylthiomethyl]-1,4-dihydropyridine m.p. 143°–144° C.;

3-carboethoxy-5-carbomethoxy-6-methyl-4-(m-chlorophenyl)-2-[(1-methoxy-1-cyclohexyl)thiomethyl]-1,4-dihydropyridine; (amorphous solid).

3-carboethoxy-5-nitro-6-methyl-4-(m-nitrophenyl)-2-[(1-phenyl-1-methoxyethyl)thiomethyl]1,4-dihydropyridine;

3,5-dicarbomethoxy-4-(m-trifluoromethylphenyl)-2-[1-ethoxy-l-(3-pyridyl)methylthiomethyl]-6-methyl-1,4-dihydropyridine.

EXAMPLE 2

0.205 ml of triethylamine (1,476 mmol.) and 0.133 ml of methoxyethoxymethylchloride (MEM-Cl) (1,476 mmol.) are added to a solution of 3,5-dicarboethoxy-6-methyl-2-mercaptomethyl-4-(m-nitrophenyl)-1,4-dihydropyridine (400 mg, 0,984 mmol.) in anhydrous THF. The mixture is left to react for 30' at room temperature under nitrogen atmosphere. The reaction mixture is diluted with a mixture of ethyl acetate-water 1:1 (100 ml) and the phases are separated: the organic phase is washed with a 5% sodium bicarbonate solution (3×20 ml) and water (2×20 ml), dried on sodium sulphate, filtered and the solvent is evaporated under reduced pressure, yielding 422 mg of 3,5-dicarboethoxy-6-methyl-2-(methoxyethoxy-methylthiomethyl)-4-(m-nitrophenyl)-1,4-dihydropyridine, as a glassy yellow oil.

NMR ($\delta$, CDCl$_3$) 1.20 (t, 6H) 2.31 (s, 3H), 3.30 (s, 3H), 3.70 (m, 4H), 4.00 (s, 2H), 4.10 (q, 1H), 4.70 (s, 2H), 5.10 (s, 1H), 7.70 (m, 5H).

EXAMPLE 3

A solution of 3,5-dicarboethoxy-6-methyl-4-(m-nitrophenyl)-2-mercaptomethyl-1,4-dihydropyridine (300 mg; 0,738 mmol.) in anhydrous THF (3 ml), at a temperature of 0° C. under nitrogen atmosphere, is added with 29 mg of sodium hydride (60% dispersion in mineral oil, 0,738 mmol.). The suspension is stirred until the sodium hydride is fully dissolved (about 15 minutes). A solution of methylthiomethylchloride (0,073 ml; 0,086 mmol.) in THF (1 ml) is then added dropwise at 0° C. to the above solution. When the addition is complete, the solution is stirred for 1.5 hours, at room temperature. After 1.5 hours the solution is poured in H$_2$O/ice (50 ml) and is extracted with ethyl acetate (50 ml).

The separated organic phase is washed with a 5% sodium bicarbonate aqueous solution (3×10 ml) and then with water, dried on sodium sulphate, filtered and evaporated under reduced pressure (370 ml of a yellow sticky oil) and it is purified by column chromatography (10 g of SiO$_2$; eluent hexane; ethyl acetate 9:1). 270 mg of 3,5-dicarboethoxy-6-methyl-4-(m-nitrophenyl)-2-(methyl-thiomethylthiomethyl)-1,4-dihydropyridine (yellow oil) are obtained.

NMR ($\delta$, CDCl$_3$) 1.20 (t, 6H) 2.20 (s, 3H), 2.35 (s, 3H), 3.70 (m, 4H), 4.10 (s, 2H), 4.20 (q, 4H), 5.15 (s, 1H), 7.10–8.10 (m, 5H).

Using in the procedure of examples 2 or 3 a compound selected from chloromethyl-benzylthioether, chloromethyl-phenyl ether, chloromethyl- p-chlorophenylthio ether and chloromethyl-3-pyridylether and a suitable 2-mercaptomethyl-1,4-dihydropyridine the following compounds are prepared:

3-carboethoxy-5-carbomethoxy-6-methyl-4-(o-trifluoromethyl)-2-(benzylthiomethylthiomethyl)-1,4-dihydropyridine;

3,5-dicarbomethoxy-6-methyl-4-(m-chlorophenyl)-2-(phenoxymethylthiomethyl)-1,4-dihydropyridine;

3-carboethoxy-5-carbomethoxy-6-methyl-4-(m-nitrophenyl)-2-(3-pyridyloxymethylthiomethyl)-1,4-dihydropyridine;

3-carbomethoxy-5-carboisopropoxy-6-methyl-4-(o-methylthiophenyl)-2-(p-chlorophenylthiomethylthiomethyl)-1,4-dihydropyridine.

EXAMPLE 4

A solution of 3,5-dicarboethoxy-6-methyl-2-mercaptomethyl-4-(m-nitrophenyl)-1,4-dihydropyridine (2 g; 4,92 mmol.) in anhydrous ethyl alcohol (20 ml) is added with a solution of N-hydroxymethylacetamide (0.67 g) in ethanol (5 ml). The mixture is refluxed for 72 hours in nitrogen atmosphere under stirring.

The solvent is evaporated under reduced pressure and the residue is dissolved in ethyl acetate (100 ml) and water (20 ml). The phases are separated, and the organic phase is washed several times (3×30 ml) with a 5% sodium bicarbonate solution (2×30 ml) and with water (2×30 ml), dried on sodium sulphate, filtered and the solvent is evaporated under reduced pressure, so obtaining 2.21 g of a resinous yellow oil that is purified by column chromatography (60 g of silica gel, eluent isopropyl ether/ethyl acetate 8:2). 1.41 g of 3,5-dicarboethoxy-6-methyl-2-[(N-acetamido)methylthiomethyl]-4-(m-nitrophenyl)-1,4-dihydropyridine (m.p. 127°–129° C.) are obtained.

Using in the above conditions a methylolamide selected in the group of hydroxymethylbenzamide, hydroxymethylsalicylamide, hydroxymethyl-(p-amino)- benzamide, hydroxymethylnicotinamide and a suitable 2-mercaptomethyl-1,4-dihydropyridine the following compounds are obtained:

3,5-dicarboethoxy-6-methyl-4-(m-chlorophenyl)-2-[(benzamidomethyl)thiomethyl-1,4-dihydropyridine;

3,5-dicarbomethoxy-6-methyl-4-(o-trifluoromethylphenyl)-2-[(N-salicylamido)-methylthiomethyl)-1,4-dihydropyridine;

3-carboethoxy-5-carbomethoxy-6-methyl-4-(m-nitrophenyl)-2-[(N-p-amino-benzamido)methylthiomethyl]-1,4-dihydropyridine;

3-carboethoxy-5-methoxyethoxycarbonyl-6-methyl-4-(2-methylthiophenyl)-2-(N-nicotinoyl-aminomethylthiomethyl)-1,4-dihydropyridine.

EXAMPLE 5

A solution of 3,5-dicarboethoxy-6-methyl-2-mercaptomethyl-4-( m-nitrophenyl)-1,4-dihydropyridine in MeOH (25 ml) is added with a 37% formaldehyde aqueous solution (6 ml, 79 mmol.). The obtained solution is refluxed for 1.5 hours. The solvent is evaporated under reduced pressure and the residue is dissolved in ethyl acetate (50 ml). The organic phase is washed (3×60 ml), separated, dried on $Na_2SO_4$, filtered and the solvent is evaporated under reduced pressure; the oily residue is crystallized from isopropyl ether, obtaining 3 g of 3,5-dicarboethoxy-4-(m-nitro-phenyl)-6-methyl-2-(hydroxymethylthiomethyl)-1,4-dihydropyridine, m.p. 113°–114° C.

The listed 2-(hydroxymethylthiomethyl)-6-methyl-1,4-dihydropyridine were also obtained:
3-carboethoxy-5-carbomethoxy-4-(m-nitrophenyl);
3,5-dicarboethoxy-(m-chlorophenyl);
3,5-dicarbomethoxy-(m-methoxyphenyl).

Following the same procedure, but using methyl glyoxylate, the following compound was obtained:
3,5-dicarboethoxy-6-methyl-4-(m-nitrophenyl)-2-[(1-methoxycarbonyl-1-hydroxy)-methylthiomethyl]-1,4-dihydropyridine. Yellow oil.
NMR ($\delta$, $CDCl_3$) 1.20 (t, 6H) 2.34 (s, 3H), 3.40 (sb, 1H, OH), 3.75 (s, 3H), 4.10 (q, 4H), 4.20 (s, 2H), 5.10 (s, 1H), 5.33 (d, 1H, CH), 7.10–8.20 (m, 5H).

EXAMPLE 6

A solution of 3,5-dicarboethoxy-6-methyl-4-[(m-nitro)phenyl]-2-hydroxy-methylthiomethyl)-1,4-dihydropyridine (500 mg; 1,14 mmol.) in anhydrous THF (10 ml) at 0° C. in an inert atmosphere, is slowly added with a solution of thionyl chloride (1.368 mmol.; 0.1 ml) and anhydrous pyridine (0.097 ml; 1.197 mmol.) in anhydrous ethyl ether (10 ml). When the addition is complete the solution is warmed to the room temperature, and it is left to react for 4 hours. The mixture is diluted with ethyl acetate, and the organic phase is washed several times with a 5% sodium bicarbonate aqueous solution (3×30 ml) and water (2×20 ml), dried on sodium sulphate, filtered and evaporated to give a sticky yellow oil (550 mg) that is purified by column chromatography ($SiO_2$ 15 g; eluent hexane:ethyl acetate 85:15).

150 mg of 3,5-dicarboethoxy-6-methyl-4-[(m-nitro)-phenyl]-2-(chloromethylthiomethyl)-1,4-dihydropyridine, m.p. 157°–159° C. are obtained.

EXAMPLE 7

A solution of 3,5-dicarboethoxy-6-methyl-4-[(m-nitro)-phenyl]-2-hydroxymethylmercaptomethyl-1,4-dihydropyridine (200 mg; 0.496 mmol.) in anhydrous THF (2 ml) and formaldehyde (100 mg) in inert atmosphere at room temperature, is added with a solution of hydrochloric acid in ethyl ether (5 ml). After 16 hours the same procedure as in Example 6 has been carried out obtaining, after purification by column chromatography 170 mg of the same product obtained in example 6: 3,5-dicarboethoxy-6-methyl-4-(m-nitrophenyl)-2-(chloromethylthiomethyl)-1,4-dihydropyridine, m.p. 158°–160° C.

EXAMPLE 8

A solution of 3,5-dicarboethoxy-6-methyl-4-[(m-nitro)phenyl]-2-mercaptomethyl-1,4-dihydropyridine (200 mg; 6.67 mmol.) in anhydrous benzene (3 ml) at room temperature and under inert atmosphere, is added with 115 mg of p-nitrobenzaldehyde (0.738 mmol.) and a catalytic amount of p-toluensulphonic acid. After 16 hours at room temperature the reaction mixture is evaporated under reduced pressure and the residue (500 mg) is purified by column chromatography ($SiO_2$, eluent hexane:ethyl acetate 7:3), to give 400 mg of 3,5-dicarboethoxy-6-methyl-4-(m-nitro- phenyl)-2-[(1-hydroxy-1-(4-nitrophenyl)methyl]-thiomethyl-1,4-dihydropyridine.
NMR ($\delta$, $CDCl_3$) 1.30 (t, 6H) 2.30 (s, 3H), 4.00 (s, 2H), 4.10 (q, 4H), 4.95 (d, 1H), 5.10 (s, 1H), 5.12 (sb, 1H), 7.20–8.20 (m, 8H).

EXAMPLE 9

A solution of 3,5-dicarboethoxy-6-methyl-4-(m-nitrophenyl)-2-hydroxymethylthiomethyl)-1,4-dihydropyridine (0,5 g) in anhydrous methylene chloride (5 ml) and 4-N,N-dimethylaminopyridine (1,5 g) is added with 1.3 ml of acetic anhydride (1.2 molar eq.), at a temperature of $-10°$ C. The solution is stirred for 1 hour, while the temperature is raised to 20° C. The solvent is evaporated under reduced pressure, the residue is diluted with ethyl acetate and the organic phase is washed with a 2N sulphuric acid aqueous solution (2×10 ml) and then with water (3×20 ml).

400 mg of 3,5-dicarboethoxy-6-methyl-4-(m-nitrophenyl)-2-(acetoxymethylthiomethyl)-1,4-dihydropyridine (m.p. 118°–121° C.) are obtained.

Using the same procedure, the following 2-(acetoxymethylthiomethyl)-6-methyl-1,4-dihydropyridine were obtained:
3-carboethoxy-5-carbomethoxy-4-(m-nitrophenyl) m.p. 111°–114° C.;
3,5-dicarboethoxy-(m-chlorophenyl);
3,5-dicarbomethoxy-(m-methoxyphenyl).

EXAMPLE 10

A solution of 3,5-dicarboethoxy-6-methyl-4-(m-nitrophenyl)-2-(acetoxymethylthiomethyl)-1,4-dihydropyridine (1 g) in 1,2-dichloroethane (10 ml) is added with a solution of m-chloroperbenzoic acid (1 molar eq.) in 1,2-dichloroethane (2 ml) at a temperature of $-10°$ C. Finally it is filtered and the organic phase is washed first with a 5% sodium thiosulphate aqueous solution (3×5 ml) and then with a 5% sodium bicarbonate aqueous solution. After drying on sodium sulphate and concentration under vacuum, 900 mg of 3,5-dicarboethoxy-6-methyl-4-(m-nitrophenyl)-2-(acetoxymethylsulphinylmethyl) -1,4-dihydropyridine, (m.p. 113°–115° C.) are obtained.

EXAMPLE 11

A solution of 3,5-dicarboethoxy-6-methyl-4-(m-nitrophenyl)-2-(acetoxymethylthiomethyl)-1,4-dihydropyridine (1 g) in methanol (20 ml) is added with a methanol solution (6 ml) of m-chloroperbenzoic acid (2 molar eq.), keeping the temperature at −10° C. and in inert atmosphere. When the addition is over, the temperature is raised to +15° C. and stirring is continued for 30′.

The solution is then concentrated to a small volume and the residue is diluted with methylene and water. The phases are separated and the organic phase is washed first with 5% sodium thiosulphate aqueous solution (3×10 ml) and then with 5% sodium bicarbonate aqueous solution (3×10 ml). After drying on sodium sulphate, filtration and evaporation under a reduced pressure, a clear yellow oil (0,98 g) of 3,5-dicarboethoxy-6-methyl-4-(m-nitrophenyl)-2-(acetoxymethylsulphonylmethyl)-1,4-dihydropyridine, is obtained.

NMR ($\delta$, CDCl$_3$) 1.20 (t, 6H) 2.00 (s, 3H), 2.30 (s, 3H), 4.05 (q, 4H), 4.80–5.20 (m, 5H), 7.20–8.20 (m, 5H).

EXAMPLE 12

A solution of 3,5-dicarboethoxy-6-methyl-2-[hydroxymethylthiomethyl]-1.4-dihydropyridine (2.56 g; 5.86 mmol.) in anhydrous methylene chloride (25 ml) kept at 0° C. in an inert atmosphere, is added with 0.957 ml of triethylamine (6.86 mmol.) and 0.657 ml of ethyl chloroformate (6.86 mmol.).

The mixture is reacted at 0° C. for 15′, then the solvent is evaporated under reduced pressure, the residue is diluted with an ethyl acetate/water 1:1 mixture (60 ml), the phases are separated and the organic one is washed several times with a 5% sodium bicarbonate aqueous solution (3×20 ml), then with water (2×20 ml), dried on sodium sulphate, filtered and evaporated under reduced pressure, to give a sticky yellow oil (3 g) that is purified by column chromatography (eluent petroleum ether:ethyl acetate 8:2). 2 g of 3,5-dicarboethoxy-6-methyl-4-[(m-nitro)-phenyl]-2-[ethoxycarbonyloxymethylthiomethyl]-1,4-dihydropyridine, m.p. 83°–85° C. are obtained.

Using in the same working conditions the acyl chlorides of 5-bromonicotic and benzoic acids, the following compounds are obtained:

3,5-dicarboethoxy-6-methyl-4-[(m-nitro)phenyl]-2-[(5-Br-nicotinoyl)-oxymethylthiomethyl]-1,4-dihydropyridine.

NMR ($\delta$, CDCl$_3$) 1.25 (t, 6H) 2.30 (s, 3H), 4.10 (s, 2H), 4.15 (q, 4H), 5.10 (s, 1H), 5.50 (s, 2H), 7.00–9.10 (m,9H).

3,5-dicarboethoxy-6-methyl-4-[(m-nitro)phenyl]-2-[benzoyloxymethylthiomethyl]-1,4-dihydropyridine.

EXAMPLE 13

A solution of 3,5-dicarboethoxy-6-methyl-4-[-m-nitro)phenyl]-2-hydroxymethylthiomethyl]-1,4-dihydropyridine (0.1 g; 0.23 mmol.), in anhydrous THF (1.5 ml) at 0° C. in an inert atmosphere is added with 69 mg of carbonyldiimidazole (0.43 mmol.) and the mixture left under stirring for 30 minute. The mixture is then diluted with ethyl acetate (30 ml); the organic phase is washed with water (3×10 ml), dried on Na$_2$SO$_4$, filtered and evaporated under reduced pressure, to give 3,5-dicarboethoxy-6-methyl-4-[(m-nitro)-phenyl]-2-[(imidazol-1-ylcarbonyloxymethyl)thiomethyl]-1,4-dihydropyridine as a yellow oil (120 mg).

NMR ($\delta$, CDCl$_3$) 1.20 (t, 6H) 2.30 (s, 3H), 4.05 (q, 4H), 4.10 (s, 2H), 4.50 (s, 2H), 5.10 (s, 1H), 7.00–8.20 (m, 8H).

EXAMPLE 14

A solution of 3,5-dicarboethoxy-4-(m-nitrophenyl)-6-methyl-2-(hydroxymethylthiomethyl)-1,4-dihydropyridine (1,0 g; 2,29 mmol.) in THF (10 ml) at room temperature and under inert atmosphere is added with 377 mg of p-aminobenzoic acid (2.75 mmol). The mixture is left to react for 2 hours. The formed dicyclohexylurea is filtered, the mixture is diluted with ethyl acetate/water 1:1 (100 ml). The phases are separated and the organic one is washed several times with a 5% sodium bicarbonate aqueous solution (3×20 ml) and with water (2×20 ml). After separation, drying on sodium sulphate, filtration and evaporation to dryness, 1.15 g of 3,5-dicarboethoxy-6-methyl-4-(m-nitrophenyl)-2-(p-aminobenzoyloxy-methylthiomethyl)-1,4-dihydropyridine, are obtained.

NMR ($\delta$, CDCl$_3$) 1.20 (t, 6H), 1.33 (s, 3H), 3.95 (s, 2H), 4.00 (q, 4H), 4.50 (m, 2H), 5.00 (s, 1H), 6.90–8.20 (m, 11H).

EXAMPLE 15

A solution of 3,5-dicarboethoxy-4-(m-nitrophenyl)-6-methyl-2-mercaptomethyl-1,4-dihydropyridine (mg 300), formaldehyde (37%); $\mu$l 90) and piperidine ($\mu$87) in ethanol (ml 3) is stirred at 40° C. under nitrogen atmosphere, for 24 hrs. After evaporation at reduced pressure the residue is purified by chromatography (SiO$_2$ 9 g eluent diisopropyl ether/ hexane 60/40) to give 2-(N-piperidinylmethylthiomethyl)-3,5-dicarboethoxy-4-(m-nitrophenyl)-6-methyl-1,4-dihydropyridine as a yellow oil.

NMR ($\delta$, CDCl$_3$) 1.00–1.80 (m, 12H); 2.30–2.70 (m, 7H); 3.70–4.20 (m, 8H); 5.00 (1H, m); 7.00–8.20 (m, 5H).

EXAMPLE 16

A mixture of benzaldehyde (4 ml 0.74), anthranilic acid (g 1) and molecular sieves 4A (g 2) in benzene (ml 7) is refluxed for 30 hours, then, after cooling to room temperature, 3,5-dicarboethoxy-4-(m-nitrophenyl)-6-methyl-2-mercaptomethyl-1,4-dihydropyridine (g 2.5) is added thereto and the mixture is stirred for further 24 hours at room temperature under nitrogen atmosphere.

The precipitate is collected by filtration and triturated with ethyl ether to give pure 3,5-dicarboethoxy-6-methyl-4-(m-nitrophenyl)2-[N-(2-carboxyphenyl)amino-1-phenylmethylthiomethyl]-1,4-dihydropyridine, m.p. 105°–107° C., (g 2).

EXAMPLE 17

A mixture of 3,5-dicarboethoxy-6-methyl-4-(-m-nitrophenyl)-2-(chloromethylthiomethyl)-1,4-dihydropyridine (mg 200) and potassium thioacetate (mg 160) in THF (ml 2) is stirred at 0° C., under nitrogen atmosphere, for 18 hours.

The reaction is diluted with iced water (ml 10) and extracted with ethyl ether (3×10 ml). The organic phase is washed with water (3×5 ml), dried (Na$_2$SO$_4$ and concentrated in vacuum. The residue is purified by chromatography (SiO$_2$ g 6; eluent hexane/ethyl acetate 90/10) to give 3,5-dicarboethoxy-6-methyl-4-(-m-nitrophenyl)-2-(acetylthiomethylthiomethyl)-1,4-dihydropyridine; amorphous solid (mg 60).

NMR ($\delta$, CDCl$_3$) 1.020 (t, 6H, 2.00 (s,3H)); 2.3 (s, 3H) 4.10 (q, 4H); 4.20–4.40 (m, 4H); 5.00 (s, 1H); 7.10–8.20 (m, 5H).

We claim:

1. A compound of formula I

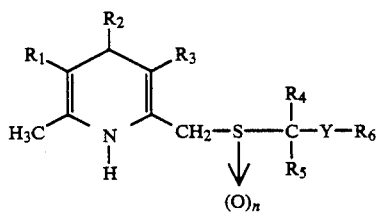

wherein:

$R_1$ is $COOR_7$;

$R_2$ is selected from the group consisting of:
 (a) phenyl unsubstituted or substituted with at least one substitutent selected from the group consisting of $C_1$–$C_6$-alkoxy, halo-$C_1$–$C_6$alkyl, $C_1$–$C_6$-alkyl, halo-$C_1$–$C_6$-alkoxy, halogen, nitro, cyano, and $C_1$–$C_6$-alkylthio;

$R_3$ is $COOR_7$;

one of $R_4$ and $R_5$ is hydrogen and the other is selected from the group consisting of:
 (a) phenyl unsubstituted or substituted with at least one substituent selected from the group consisting of halogen, nitro, $C_1$–$C_6$-alkoxy, and hydroxy; and
 (b) $COOR_7$;

$YR_6$ is selected from the group consisting of:
 (a) OH;
 O—$R_a$;
 (c) O—$R_b$;
 (d) O—$R_c$;
 (e) S—$R_a$;
 (f)

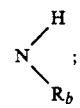

( g)

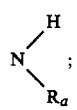

and
(h)

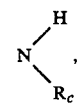

wherein
$R_a$ is a $C_1$–$C_6$ alkyl group unsubstituted or substituted with at least one $C_1$–$C_6$ alkoxy group;
$R_b$ is an acyl group selected from the group consisting of $C_2$–$C_{12}$ alkanoyl, benzoyl, p-aminobenzoyl, o-hydroxybenzoyl, nicotinoyl, 5-bromonicotinoyl, and imidazolyl-1-carbonyl; and
$R_c$ is $C_1$–$C_6$ alkoxycarboxyl group;
$R_7$ is selected from the group consisting of:
 (a) a $C_1$–$C_6$-alkyl group unsubstituted or substituted with at least one substituent selected from the group consisting of hydroxy and $C_1$–$C_6$-alkoxy;
 (b) a $C_3$–$C_6$-alkyl group; and
 (c) phenyl;
n is 0, 1 or 2, with the proviso that, when $YR_6$ is S—$R_a$, n is zero.

2. A compound according o claim 1, wherein $R_2$ is selected from the group consisting of m-nitrophenyl, o-chlorophenyl, m-chlorophenyl, m-trifluoroethylphenyl, and o-methylthiophenyl.

3. A compound according to claim 1, which is:
3,5-dicarboxylic-6-methyl-4-(m-nitrophenyl)-2-[(methoxycarbonyl-hydroxymethyl)thiomethyl]-1,4-dihydropyridine.

4. The compound:
3,5-dicarboethoxy-6-methyl-4-(m-nitrophenyl)-2-[N-(2-carboxyphenyl) -amino-phenylmethylthiomethyl]-1,4-dihydropyridine.

5. A pharmaceutical composition for the treatment of hypertension, comprising an inert carrier and an effective amount of the compound of any one of claims 1, 2, 3 and 4.

6. A method of treating hypertension, comprising administering to a patient suffering from hypertension an effective amount of the compound of any one of claims 1, 2, 3 and 4.

* * * * *